(12) United States Patent
Godin (10) Patent No.: US 11,571,289 B2
(45) Date of Patent: Feb. 7, 2023

(54) MEDICAL DEVICE AND METHOD OF IMPLANTING GASTROESOPHAGEAL ANTI-REFLUX AND OBESITY DEVICES IN AN ESOPHAGUS

(71) Applicant: Biomedix S.A., Geneva (CH)

(72) Inventor: Norman Godin, Geneva (CH)

(73) Assignee: BIOMEDIX S.A., Geneva (CH)

( * ) Notice: Subject to any disclaimer, the term of this patent is extended or adjusted under 35 U.S.C. 154(b) by 68 days.

(21) Appl. No.: 16/610,612

(22) PCT Filed: May 31, 2018

(86) PCT No.: PCT/US2018/035312
§ 371 (c)(1),
(2) Date: Nov. 4, 2019

(87) PCT Pub. No.: WO2018/222819
PCT Pub. Date: Dec. 6, 2018

(65) Prior Publication Data
US 2020/0060805 A1     Feb. 27, 2020

Related U.S. Application Data

(60) Provisional application No. 62/513,572, filed on Jun. 1, 2017, provisional application No. 62/629,216, filed on Feb. 12, 2018.

(51) Int. Cl.
*A61F 2/04* (2013.01)
*A61F 5/00* (2006.01)
(Continued)

(52) U.S. Cl.
CPC .............. *A61F 2/04* (2013.01); *A61F 5/0079* (2013.01); *A61F 5/0089* (2013.01);
(Continued)

(58) Field of Classification Search
CPC .................. A61F 2/04; A61F 2002/044; A61F 2002/045; A61F 5/0076; A61F 5/0079;
(Continued)

(56) References Cited

U.S. PATENT DOCUMENTS 5,354,279 A   10/1994  Hofling
5,437,291 A   8/1995   Pasricha et al.
(Continued)

OTHER PUBLICATIONS

Sioulas et al. Self-expandable metal stents for achalasia: Thinking out of the box!. World J Gastrointest Endosc. Jan. 16, 2015 (retrieved on Jul. 16, 2018). Retrieved from the internet: <URL: https://f6publishing.blob.core.windows.neV31 ccfa63-0dbd-4146-960f-31 b05d3f0b8d/WJGE-7-45 .pdf>. entire document.
(Continued)

*Primary Examiner* — Jennifer Dieterle
*Assistant Examiner* — Rebecca Lynee Zimmerman
(74) *Attorney, Agent, or Firm* — Debora Plehn-Dujowich; Eckert Seamans Cherin & Mellott, LLC (57) ABSTRACT

A method of preventing contraction and peristaltic wave action of an esophagus in which a GARD is placed, preventing displacement of the GARD towards or into a stomach, the method comprising injecting botulinum toxin very precisely in the muscular layer of the esophageal wall at the level where the GARD is or will be placed. A system comprising a catheter having one or two expandable balloon (s) which carries guide needle catheters that can pierce the esophageal wall and reach precisely the muscular layer of the wall of the esophagus, the needles used to inject the toxin at precisely the exact location in the esophageal wall in relationship with the GARD device to block esophageal peristalsis locally.

6 Claims, 10 Drawing Sheets

(51) Int. Cl.
*A61K 38/48* (2006.01)
*A61B 17/00* (2006.01)
*A61M 25/10* (2013.01)
*A61M 25/00* (2006.01)

(52) U.S. Cl.
CPC .............. *A61K 38/4893* (2013.01); *A61B 2017/00827* (2013.01); *A61F 2002/044* (2013.01); *A61F 2220/0075* (2013.01); *A61M 25/1002* (2013.01); *A61M 25/1011* (2013.01); *A61M 2025/0087* (2013.01); *A61M 2202/049* (2013.01); *A61M 2210/105* (2013.01)

(58) Field of Classification Search
CPC ........ A61F 5/0089; A61B 2017/00827; A61K 38/4893
See application file for complete search history.

(56) References Cited

U.S. PATENT DOCUMENTS

| | | | | |
|---|---|---|---|---|
| 8,870,937 | B2* | 10/2014 | Ginn | .............. A61B 17/0057 623/1.12 |
| 2004/0148034 | A1 | 7/2004 | Kagan et al. | |
| 2008/0082159 | A1 | 4/2008 | Tseng et al. | |
| 2008/0249533 | A1 | 10/2008 | Godin | |
| 2011/0118650 | A1* | 5/2011 | Nihalani | .............. A61F 5/0076 604/9 |
| 2014/0249464 | A1* | 9/2014 | Godin | .............. A61B 1/2736 604/8 |

OTHER PUBLICATIONS

Pasricha Pankaj J. et al, "Intrasphincteric Botulinum Toxin for the Treatment of Achalasia", The New England Journal of Medicine, US, (Mar. 23, 1995), vol. 332, No. 12, pp. 774-778.

Van Hoeij Froukje B. et al, "Complications of botulinum toxin injections for treatment of esophageal motility disorders+ : Complications of esophageal botox injections", Diseases of the Esophagus, AU, ISSN 1120-8694, (Jun. 1, 2016).

Storr Martin et al, "Treatment of symptomatic diffuse esophageal spasm by endoscopic injections of botulinum toxin: A prospective study with long-term follow-up", Gastrointestinal Endoscopy, NL, (Dec. 1, 2001), vol. 54, No. 6, pp. 754-759.

EESR for Application No. 18809683.8 dated May 28, 2021.

* cited by examiner

FIG. 11

MEDICAL DEVICE AND METHOD OF IMPLANTING GASTROESOPHAGEAL ANTI-REFLUX AND OBESITY DEVICES IN AN ESOPHAGUS

CROSS-REFERENCE TO RELATED APPLICATIONS

This application is a U.S. National Stage Application under 35 U.S.C. § 371 of PCT International Application No. PCT/US2018/035312, entitled "MEDICAL DEVICE AND METHOD OF IMPLANTING GASTROESOPHAGEAL ANTI-REFLUX AND OBESITY DEVICES IN AN ESOPHAGUS," filed on May 31, 2018, which claims the benefit of U.S. provisional application No. 62/513,572, filed on Jun. 1, 2017, and 62/629,216, filed on Feb. 12, 2018, which are claimed and are hereby incorporated by reference.

BACKGROUND OF THE INVENTION

This invention relates to the field of medical devices, particularly medical devices relating to gastroenterology, and more specifically to methods of implanting gastroesophageal anti-reflux devices and or obesity devices in an esophagus.

GARDs are thin walled tubular medical devices placed in the esophagus which are placed in the esophagus or extend from the esophagus into the stomach with a top ring that is calibrated precisely to the millimeter to the diameter of the esophagus with a calibration basket that is passed through the working channel of the endoscope at the level of the lower third of the body of the esophagus under visual control of the gastroscope to determine the diameter of the esophagus once opened. The calibration basket is opened up to the point where the three arms of the calibration basket are in contact with the wall of the esophagus, the size is marked on the handle of the calibration basket, then the calibration basket is closed, removed from the working channel of the gastroscope and is reopened to the same opening outside the patient. In order to determine the appropriate size ring, usually between 20 mm and 30 mm of diameter, the calibration basket is reopened to the same size measured in the esophagus and a calibration card with sizing holes is used to determine to the millimeter the size of the GARD device needed for a given patient.

The Diagnosis and Management GARD ("DM-GARD") has a tube in the range of 5 cm to 10 cm, preferably 7.5 cm, long with a 2.5 cm long ring for a total length of 7.5 to 12.5 cm, preferably 10 cm, wherein the thin-walled tube will fold onto itself during reflux back-pressure and will straighten back into the original position spontaneously when the back-pressure stops and is indicated to diagnose gastroesophageal reflux disease (GERD) not responding to PPIs, defined as "Refractory GERD." As the DM-GARD is a mechanical device, all refluxate that is acid, bile, mixed, and/or gastric enzymes that reflux form the stomach into the esophagus will be blocked while Proton Pump Inhibitors (PPIs) which are widely used to treat GERD will only help to treat acid reflux but do poorly with other kinds of reflux. Also, we now know that the volume of reflux is the same when the patients take PPIs even when the content is less acid. Up to 30% of patients who have GERD do not respond well or not at all to PPIs and are diagnosed as having Refractory GERD. These patients have no treatment as they do not respond to PPIs as a rule. Surgeons avoid operating on patients who do not respond to PPIs, fearing that the patients will be worse off after surgery as the diagnosis is unclear. Also, about 1% of the population has Laryngo-Pharyngeal Reflux (LPR) which is reflux content reaching the larynx causing chronic sore throat, chronic cough, voice changes affecting quality of life and often careers where oral communication is important. In many cases, high dose PPIs corresponding to the double of a normal 40 mg Nexium (esomeprazole) pill will be prescribed to these LPR patients for 8 to 12 weeks with no effect on the LPR symptoms. pH-impedance tests can demonstrate reflux in these patients if there is high volume but the quality of the refluxate is poorly changed with PPIs, particularly when there is bile reflux. The DM-GARD can be expected to help these patients when implanted for longer periods of time as the device is purely mechanical and stops all refluxate mechanically without distinction of pH or volume of the refluxate content.

A DM-GARD placed temporarily for less than a month can help the doctor and patient decide if a longer, slightly more invasive device, called the Therapeutic GARD, should be placed in a given patient for a much longer period of time. The GARD family of devices is the only method that allows a trial period with a temporary device, namely the DM-GARD, to help determine if the patient should be managed with the DM-GARD and help avoid implanting a device that would not be helpful as can happen in the case of surgery or other non-medication based treatments for GERD. The main difference between the temporary DM-GARD and the Therapeutic GARD is that the DM-GARD has a thicker ring with a nitinol helical spring as described in U.S. Pat. No. 9,572,701 dated Feb. 21, 2017 while the Therapeutic GARD has a much thinner ring that can incorporate in the wall of the esophagus as described in U.S. Provisional application No. 62/629,216 filed Feb. 12, 2018.

The OB-GARD has tubes longer than 7.5 cm, usually from 10 cm to more than 30 cm and reaching well into the stomach which, in addition of blocking reflux, will force patients to eat small quantities at the time, chew their food better, and eat more slowly, leading to earlier satiety as the food passes through the length of the tubes and helping the patients to lose weight with appropriate diets. Longer tubes reaching through the stomach can reversibly mimic the second most common bariatric operation, namely the "sleeve" gastrectomy, where three quarters of the stomach are definitively removed along the greater curvature of the stomach, leaving a "sleeve" along the lesser curvature of the stomach. The OB-GARD as the Therapeutic GARD will also have a thinner ring capable of integration in the esophageal wall with additional features and techniques.

The tube of the OB-GARD does not require such surgery as the OB-GARD is placed through the mouth. To keep the GARD family of devices in place, a ring at the top, or proximal end, of the device is placed in the lower third of the esophagus, more precisely in the last 5 cm of the esophagus above the Z line or esogastric junction. The presence or not of a hiatus hernia does not affect the use of the GARD family of devices as it can in other endoscopic treatments available. Even longer OB-GARDs going through the stomach into the duodenum and jejunum can be considered mimicking the effect of the most efficient present bariatric operation, namely the gastric by-pass operation as an internal tube in the duodenum and small bowel would hold the food separately from all the gastric, bowel, bile and pancreatic secretions and enzymes helping the patient lose weight, which is done presently only through major surgery in high risk morbidly obese patients.

Also, GERD will often appear when patients gain weight. Often as little as a 5 to 10 pound (approximately 3 kg to 5 kg) can be sufficient to cause severe GERD that will improve with weight loss. The GARD is the only treatment that addresses both obesity and weight loss.

However, even with very careful sizing of the ring as described above, if the ring is wide enough to keep the GARD in the esophagus, the peristaltic contractions will not automatically push the GARD in the stomach but strong peristaltic contractions of the esophagus immediately above the ring will press hard on the top part of the ring of the GARD and cause ulcers in the esophageal mucosa at the level of the ring or immediately above as these peristaltic contractions try in vain to push the GARD downwards into the stomach. These esophageal ulcers can bleed or lead to perforations. However, above these esophageal ulcers the esophagus is normal.

There is a need to prevent displacement of a GARD from its intended location in the smooth muscle area of the esophagus resulting from contractions and peristaltic wave action without causing ulcerations of the esophageal mucosa.

SUMMARY OF THE INVENTION

Figure 1:
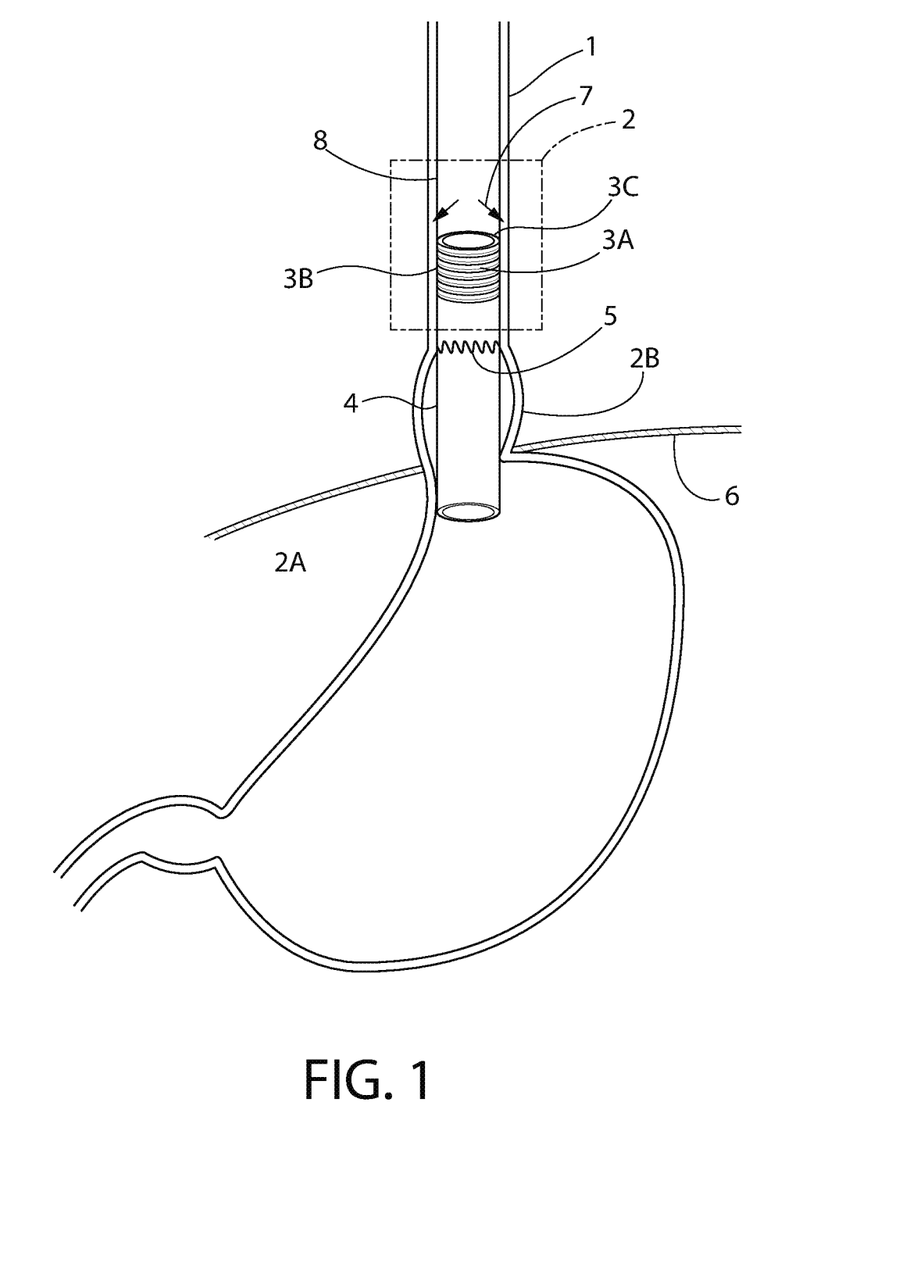
Figure 2:
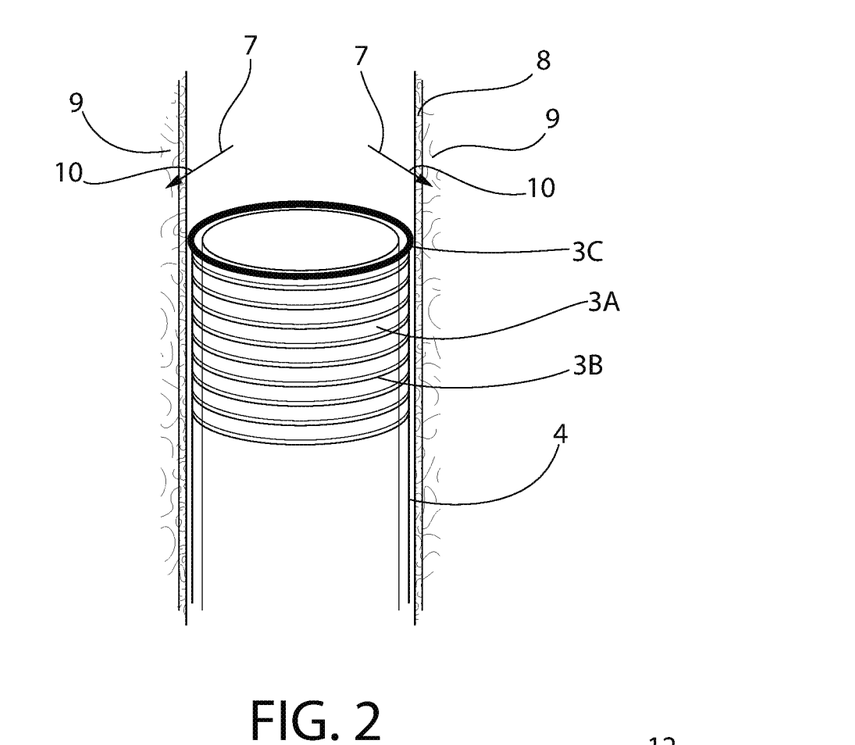

This need is addressed by the present invention which comprises in one aspect a method of blocking the contractions of the esophagus by injection of botulinum toxin in the wall of the esophagus just above the level where the GARD ring will be placed and thereby decreasing or abolishing the peristalsis of the esophagus in the area of the esophagus above where the GARD ring will be placed so that a GARD device can remain safely at its intended position for a up to a few months. In another aspect the invention comprises a system for delivery of the botulinum toxin in the wall of the esophagus at the intended location, the system comprising a balloon with a balloon expander orienting guiding tubes for an injection catheter adapted to allow precise injection of Botulinum toxin around the circumference of the esophagus at a selected depth in the esophagus to reach the muscular layer of the esophagus. A further aspect is the injection device comprising the catheter having the balloon arranged to block the catheter centrally in the esophagus when expanded so that an injection catheter will reach the esophageal wall at a selected angle for injection of the toxin at a selected depth in the muscular layer of the esophagus.

Another important advantage of botulinum toxin injection in this indication is that it has a temporary effect of at least 2 to 3 months. This is exactly the time needed to assess the efficacy of the DM GARD that will be placed between 1 week and 4 weeks and then removed. If the DM GARD helps the patient, either the Therapeutic GARD (Th-GARD) can be placed if one treats GERD or the Obesity GARD (OB-GARD) can be inserted with no need to reinject any botulinum toxin. The botulinum toxin by blocking locally peristalsis will allow integration of the Therapeutic GARD or the Obesity GARDs in the wall of the esophagus for permanent placement. As a potential side-effect of botulinum toxin injection can be some swallowing difficulties, we know that this side-effect is transient even if it turns out with the DM GARD that the patient is not helped by this therapeutic approach and the plan to place the Th-GARD or OB-GARD is not carried out.

BRIEF DESCRIPTION OF THE DRAWINGS

FIG. 1 is a cross-sectional view of a portion of human anatomy comprising an esophagus and stomach with a perspective view of a GARD device according to the invention, illustrating the position of the GARD device in the lower esophagus.

FIG. 2 is an enlarged perspective view of the ring of the GARD and the sites of injection of the botulinum toxin, illustrating a portion of an esophagus in cross-section.

FIG. 3 is a cross-sectional view from above the top of the ring as seen with the gastroscope placed in the esophagus.

FIG. 4 is a side perspective view of an injection balloon catheter with guiding tubes, before inflation at introduction, partially in cross-section.

FIG. 5A is a side perspective view of an injection balloon catheter with the balloon inflated.

FIG. 5B is a side perspective view of a balloon expander with three arms spread.

FIG. 6 is a side perspective view of an injection balloon catheter with guiding tubes, before inflation, which is a variant of FIG. 4 with a triangular balloon.

FIG. 7 is a side perspective view of the device of FIG. 6 wherein the triangular balloon is inflated and pushes up the arm of the balloon expander and the end of the guiding tube.

FIG. 8A is a side perspective view of a GARD Introducer with a Botulinum toxin injection catheter.

FIG. 8B is a cross-sectional view of the central catheter of FIG. 8A.

FIG. 8C is cross-sectional view of the central catheter of FIG. 8A with four tubes.

FIG. 9 is a side perspective view of the device of the invention with threads A,B,C pulled out to release the GARD.

FIG. 10 illustrates the device of FIG. 9 with the A,B,C threads completely pulled out of the catheter.

FIG. 11 illustrates a combination of a top small triangular, or conical balloon 23 used to spread the arms of the arm expander 22 and the guiding tube 18 and a bottom oval balloon 16 to help deploy the ring of the GARD.

DETAILED DESCRIPTION OF THE INVENTION AND PREFERRED EMBODIMENTS

Referring first to the drawings which illustrate certain preferred embodiments of the system aspect of the invention, the invention is not limited to any of the illustrated embodiments.

FIG. 1 shows the position of the GARD device in the lower esophagus 1. The tubular part of the GARD device 4 extends into the stomach 2A, below a hiatus hernia 2B which is part of stomach 2A sliding above the diaphragm 6 in the lower chest as the chest is above the diaphragm. A ring 3A having a top 3C of the GARD device includes helical spring 3B in the lower esophagus 1. The level of the Z line 5 is at the junction of gastric and esophageal mucosa. Diaphragm 6 is shown above stomach 2A. The site 7 of first injections is about 1 cm above the top 3C of the GARD ring. FIG. 1 shows a GARD device which includes a ring 3A which includes top 3C and helical spring 3B in the lower esophagus and 3C top of the ring, the ring 3A being placed above the level of the Z line 5, which is shown as an irregular line located just at the junction of gastric and esophageal mucosa in the lower esophagus 1. The tubular part 4 of the GARD device extends into stomach 2A. Diaphragm 6 is located between the lower part of the hiatus hernia 2B and the stomach 2A. The site 7 of the first injections are about 1 cm above the GARD ring 3C. Area of enlargement 8 is shown in FIG. 2.

FIG. 2 is an enlarged view of the ring 3A of the GARD and the sites 10 of injection indicated by arrows 7 of the botulinum toxin in the muscular layer 9 of the wall of the esophagus. Top 3C of ring 3A and helical spring 3B are illustrated. Mucosa and submucosa 8 and muscular layer 9 of esophagus 10 are also illustrated. The botulinum toxin is injected in the muscular layer 9, not in the mucosa or submucosa of the esophagus and not through the wall of the esophagus which is easy to do since the whole wall is only 2 to 3 mm thick. Injection of the botulinum toxin has the effect of preventing esophageal peristalsis temporarily according to the invention to assess the efficacy and safety of the GARD device and allow the placement of a more permanent device to treat Gastroesophageal Reflux Disease (GERD) and/or Obesity.

Figure 3:
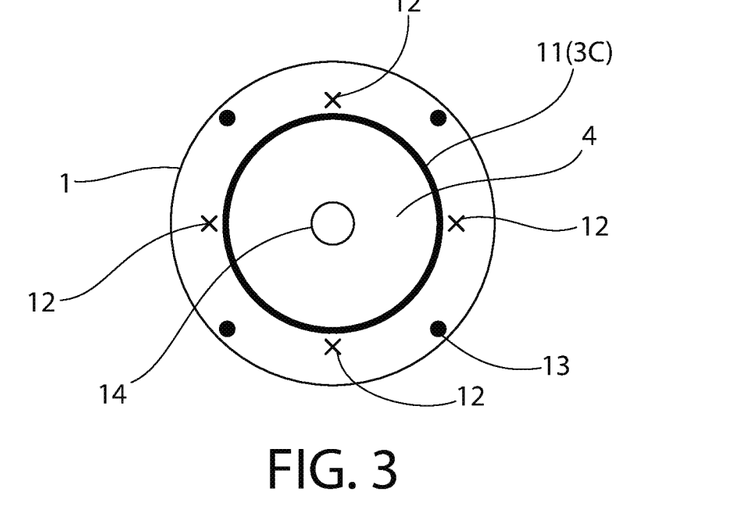

FIG. 3 is a cross-sectional view above the top of the ring as seen with the gastroscope placed in the esophagus showing the top 11 of GARD ring 3C in upper view, sites 12 of injection right above the GARD ring 3C. In this example, the injections sites are at two levels, immediately above 12 the ring 11 and 1 cm above 13 the ring 11. Injecting a two levels instead of one level is optional. The end 14 of the tubular part of the GARD is seen in perspective.

Figure 4:
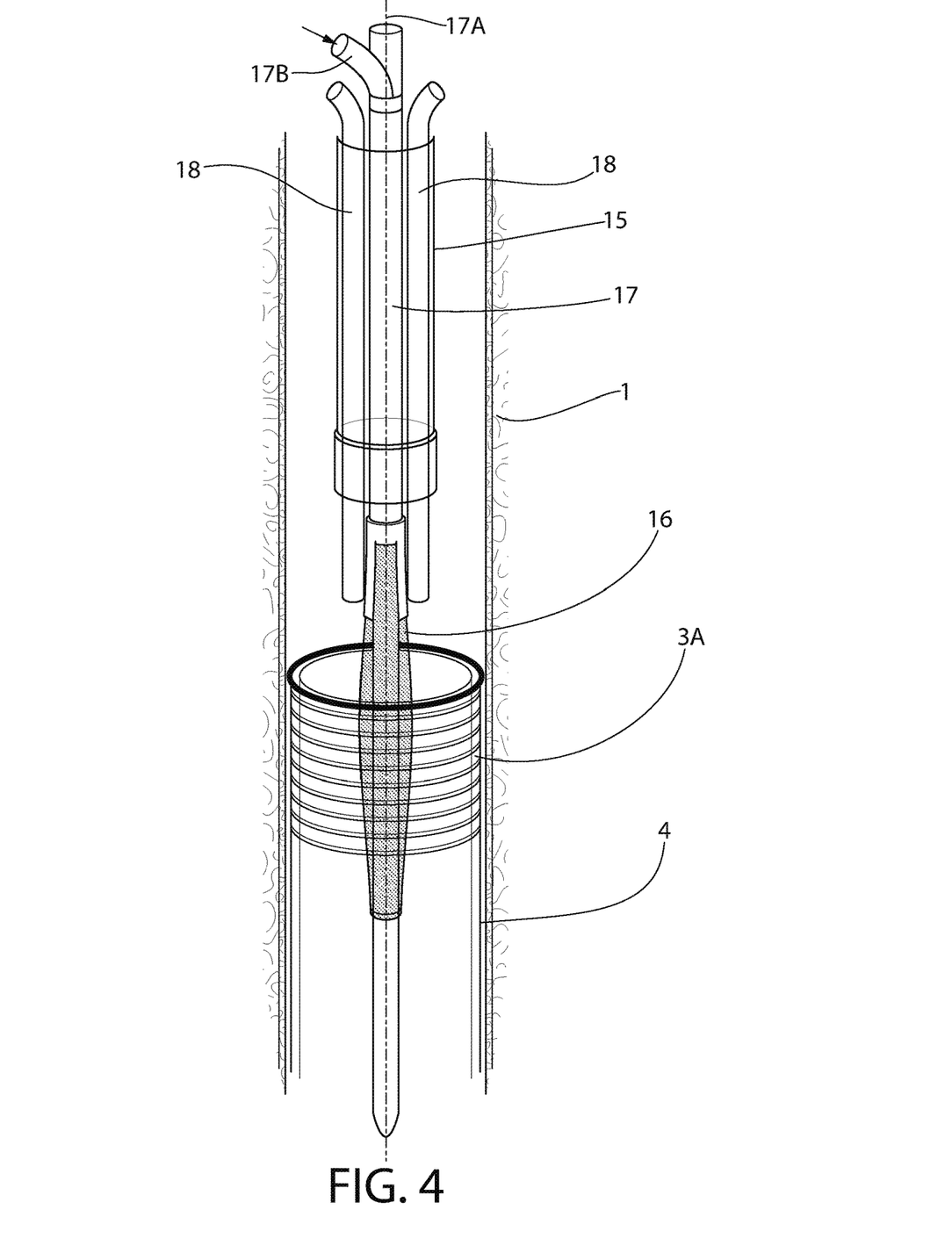
Figure 5A:
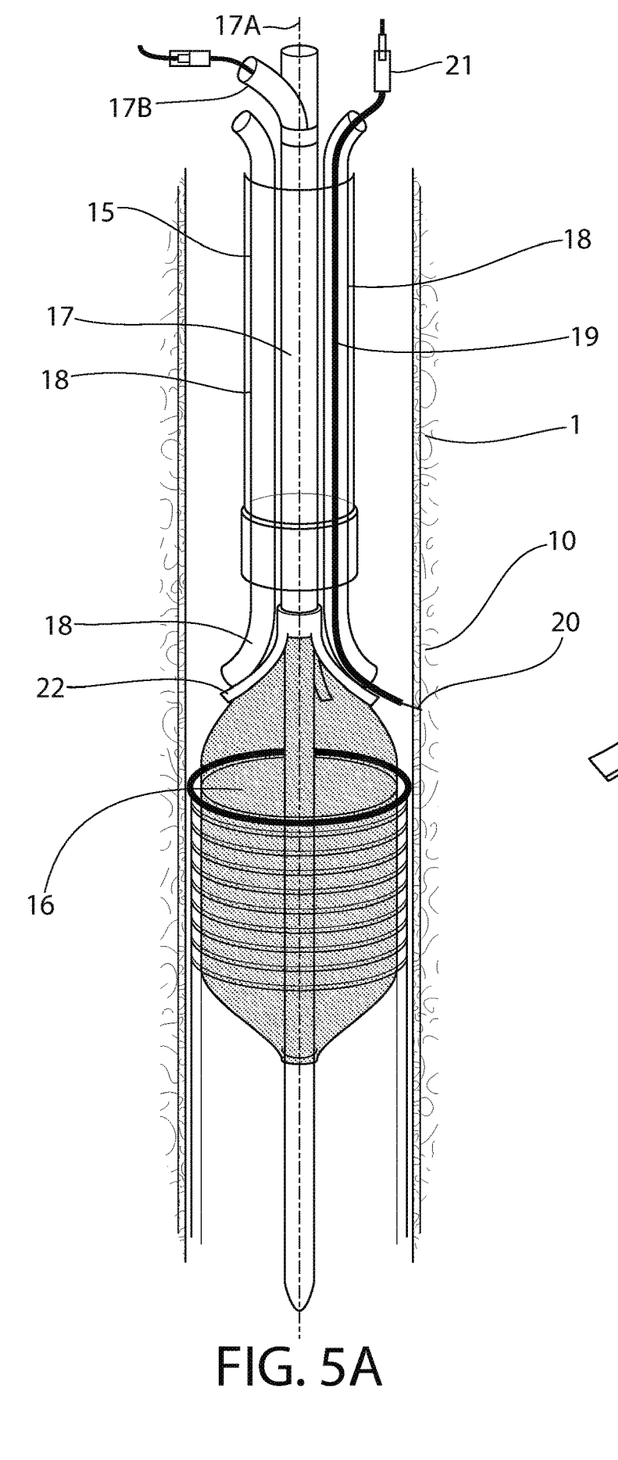

FIG. 4 illustrates an injection balloon catheter 15 with guiding tubes 18 before inflation at introduction. Two guiding tubes 18 are shown on both sides of the central catheter 17 for the central guide-wire 17A and the air inflation for the balloon 17B. A third guiding tube is in the back, not shown since hidden by the central part of the catheter 17. The balloon 16 is not inflated in this view. The tubes 18 act as lumens for guiding tubes for botulinum toxin injection catheters. In FIG. 4 the balloon catheter is placed above and inside the GARD ring to guide botulinum toxin injection at the right depth and at even distances around the circumference of the esophagus. The injection catheter can be combined with the delivery or introduction device used to place the GARD in the esophagus through the mouth as the same balloon helps deploy the GARD ring 3A and insures proper placement of the injection tubes 18 needed for precise botulinum toxin injection in the esophageal wall (See FIGS. 8A-8C, 9 and 10) or two separate catheters can be used, the first one to introduce the GARD and the second one to inject the botulinum toxin. Here in FIG. 4 the balloon catheter is separate from the delivery or introduction device. This catheter is used after the GARD device has been placed in the esophagus. The catheter has a central lumen used to place the catheter over a central guide wire 17A placed first through the mouth and esophagus into the stomach with an endoscope. Once the catheter is in position determined by distance graduations (not shown), the balloon can be inflated to help deploy the GARD ring as shown in FIG. 5A. Once the balloon has been inflated, the three arms of the balloon expander 22 will be lifted and will push up the distal end of the guiding tubes so that the injection catheter 19 placed in the guiding tube 18 can be pushed until the injection catheter makes contact with the wall of the esophagus 10 at a proper angle. The needle is then deployed and pierces the wall of the esophagus at the depth needed to reach the muscular layer of the esophagus.

FIG. 5A illustrates an injection balloon catheter 15 with inflated balloon 16 and guiding tubes 18 for injection. The injection catheter 19 includes needle 20 shown in the wall of the esophagus 1. A syringe 21 with botulinum toxin is shown ready for injection in the wall of the esophagus 1.

Figure 5B:
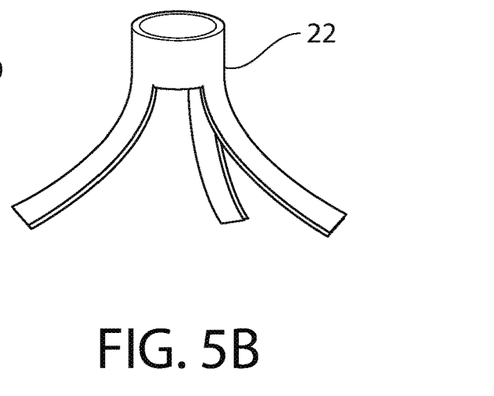

FIG. 5B illustrates a balloon expander 22 with 3 arms spread.

Figure 6:
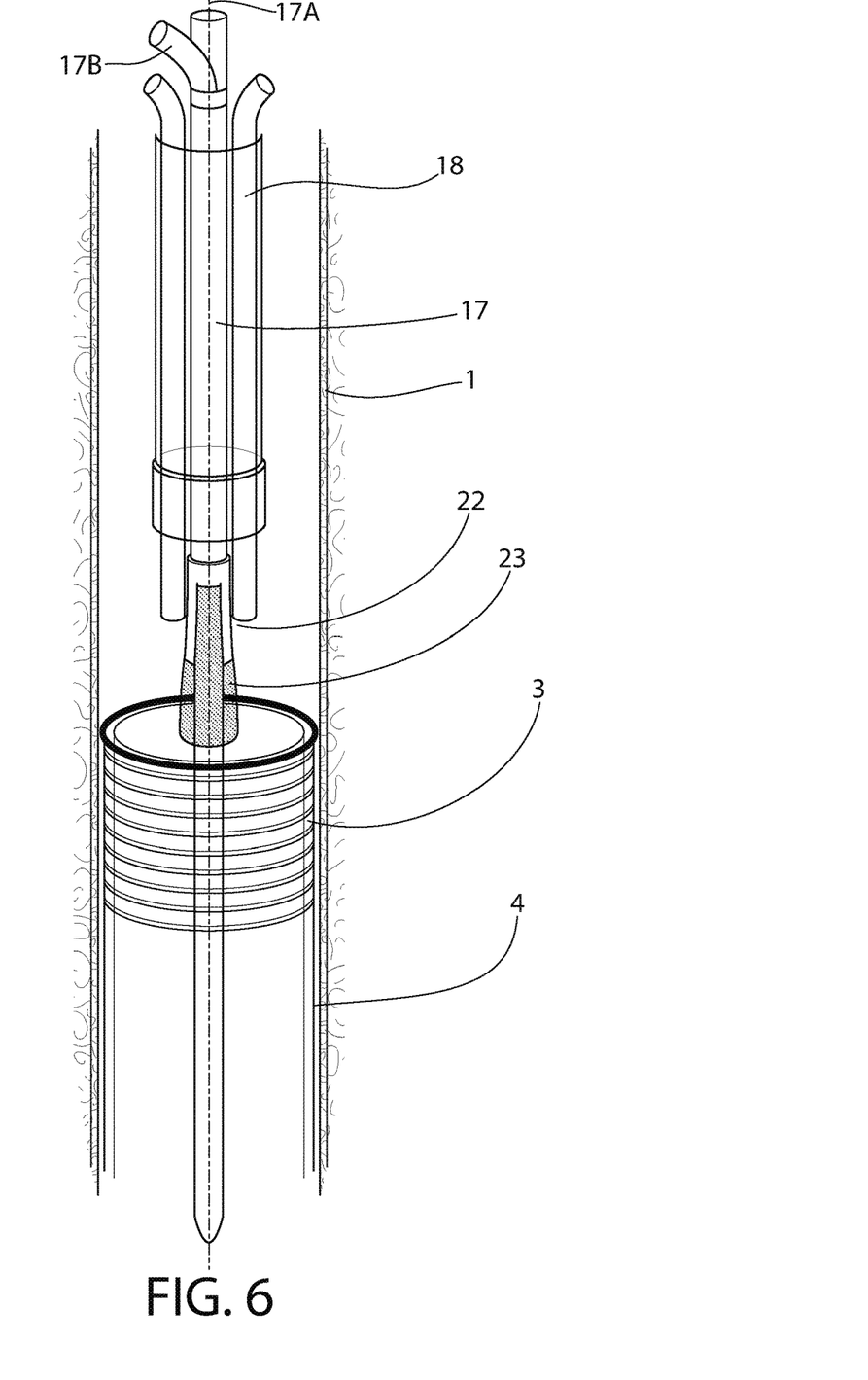
Figure 7:
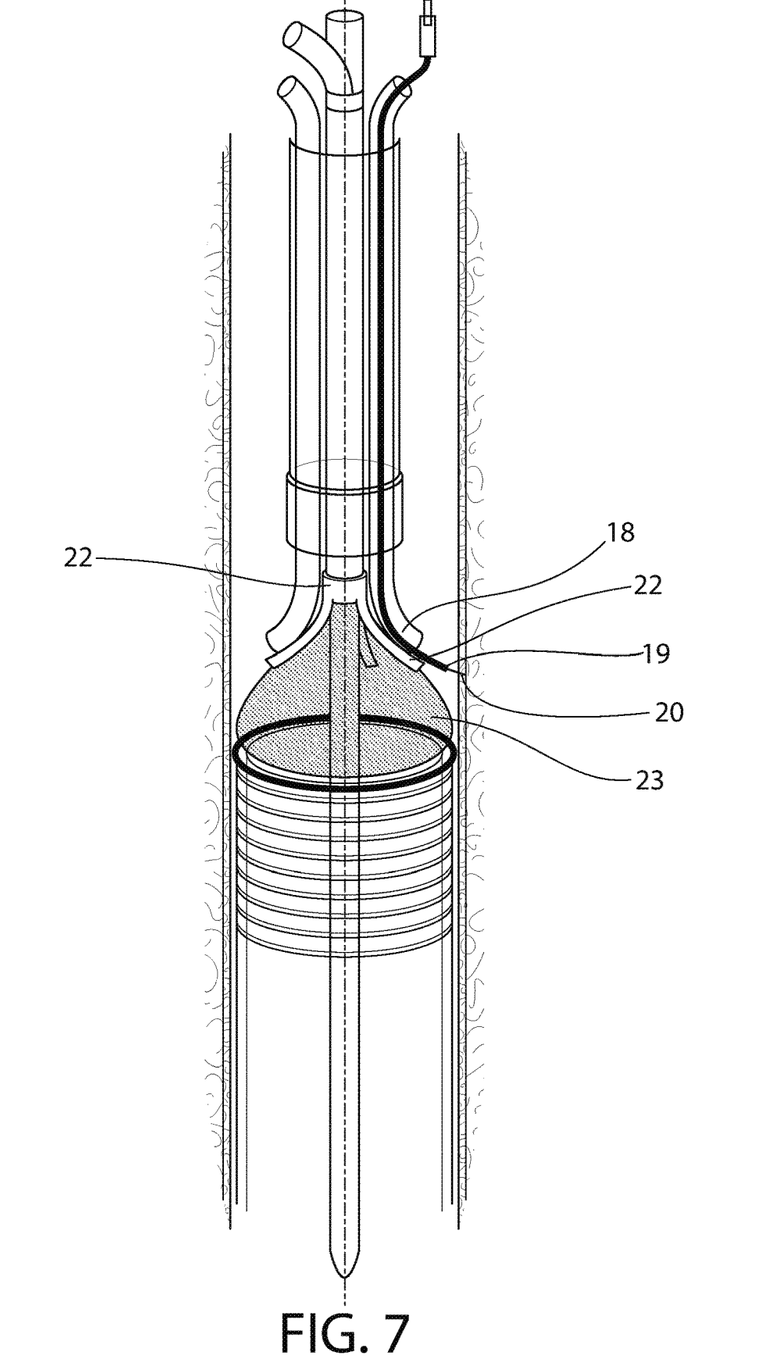

In FIGS. 6 and 7, a variant is shown, a triangular balloon 23 not yet inflated in FIG. 6 is inflated in FIG. 7 and pushes up the arm 22 of the balloon expander and the end of the guiding tube 18 at a proper angle so that the injection catheter 19 will reach the esophageal wall and the needle 20 will penetrate the esophageal wall at the desired depth reaching the esophageal wall of the esophagus.

Figure 8A:
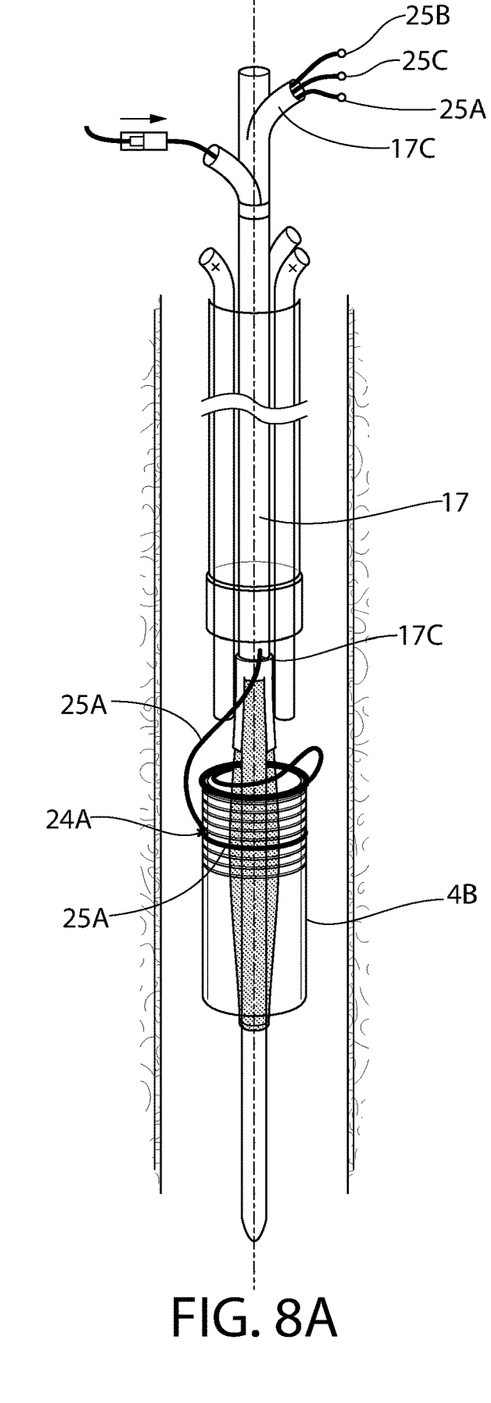

FIG. 8A illustrates a combination of the delivery catheter or GARD Introducer with the Botulinum toxin injection catheter wherein GARD ring 3D is folded during insertion and held in place with a suture 25A around the ring 3D to keep the ring folded and a knot 24A and thread 25A that then penetrates in the central catheter 17 through port 17c which is the proximal exit of the thread 25A. In a similar way, the GARD tube 4B is also folded and held in place with a suture (not shown in the bottom of the drawing) and a knot (not shown in the bottom) that will be pulled out when pulling on 25B at the top of the drawing to the left. A security thread (not shown in the bottom of the drawing) holds both knots secure and is released by pulling on 25C shown on the top of the drawing. FIG. 8A is a combination of the delivery catheter or GARD Introducer with the Botulinum toxin injection catheter. The knot 24A used is a special knot known as the "draw hitch" that can be released simply by pulling at one end, even at a distance and the knot will be released and the thread can be pulled out very easily. The security has to be pulled out first before the 2 other knots can be released.

Figure 8B:
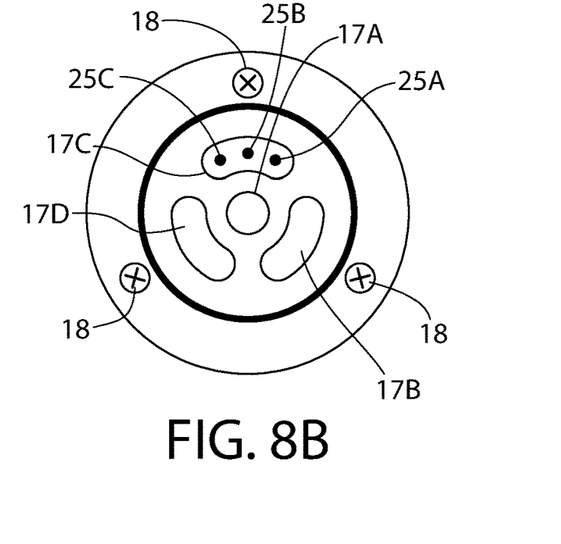
Figure 8C:
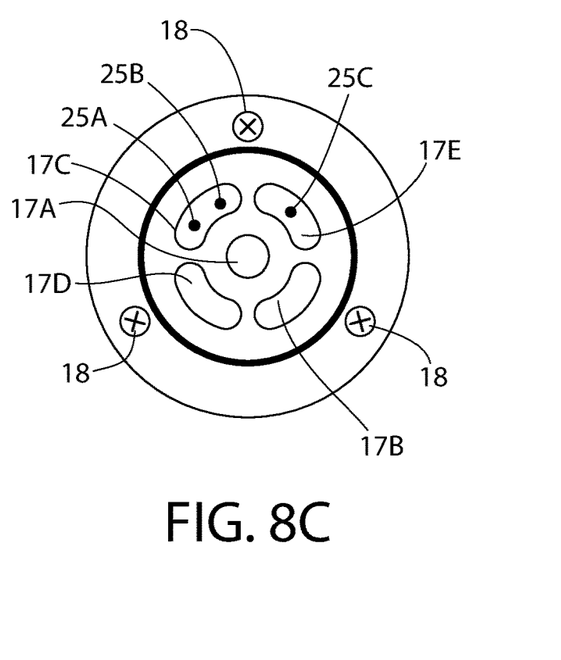

FIG. 8B is a transverse cross-sectional view of the central catheter 17, showing a lumen for the central guide wire 17A, lumen 17B for inflation of balloon and 17D is empty for possible future use, lumens for threads 25A and 25B and security thread 25C for the deployment threads of the GARD ring and tube. Guiding tubes 18 for the injection catheter are illustrated. (FIG. 8C is a variant of FIG. 8B with a fourth "bean shape" hole, 2 holes 17C and 17E are used for the threads 25A and 25B used to deploy the ring and tube of the GARD device and a security thread 25C passing through 17E.) 17B is for inflation/deflation of the oval balloon and 17D is a spare lumen that can be used if needed for inflation of the triangular balloon, see FIG. 11, when and if 2 balloons are used.

Figure 9:
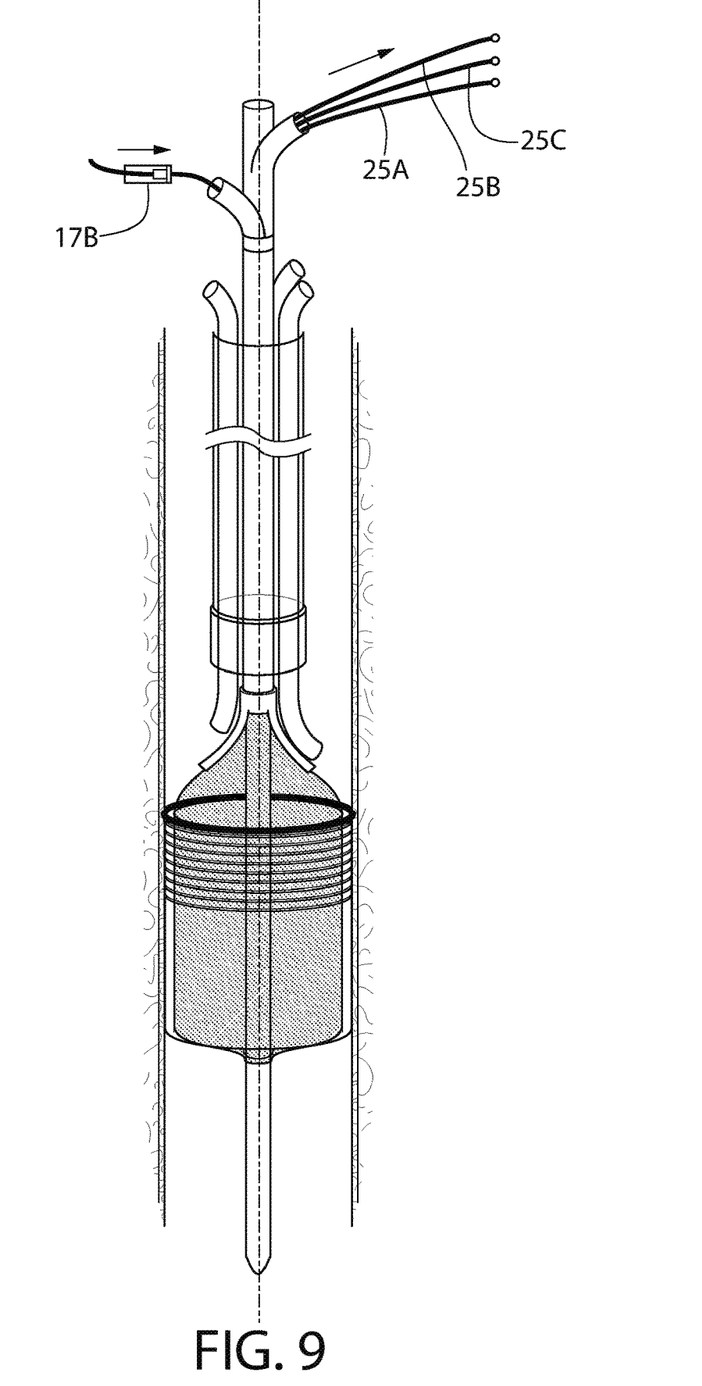

FIG. 9 shows threads 25A, B, and C pulled out to release the GARD and air injection 17B to inflate the balloon, shown inflated. In FIG. 9, the three knots are released, first the security knot 25C then 25A and 25B, and the GARD ring expands as well as the tube. The balloon is then inflated 17B to make sure that the GARD ring expands properly and reaches the wall of the esophagus. A gastroscope or fluoroscopy or both can be used optionally to check that the GARD ring is properly expanded.

Figure 10:
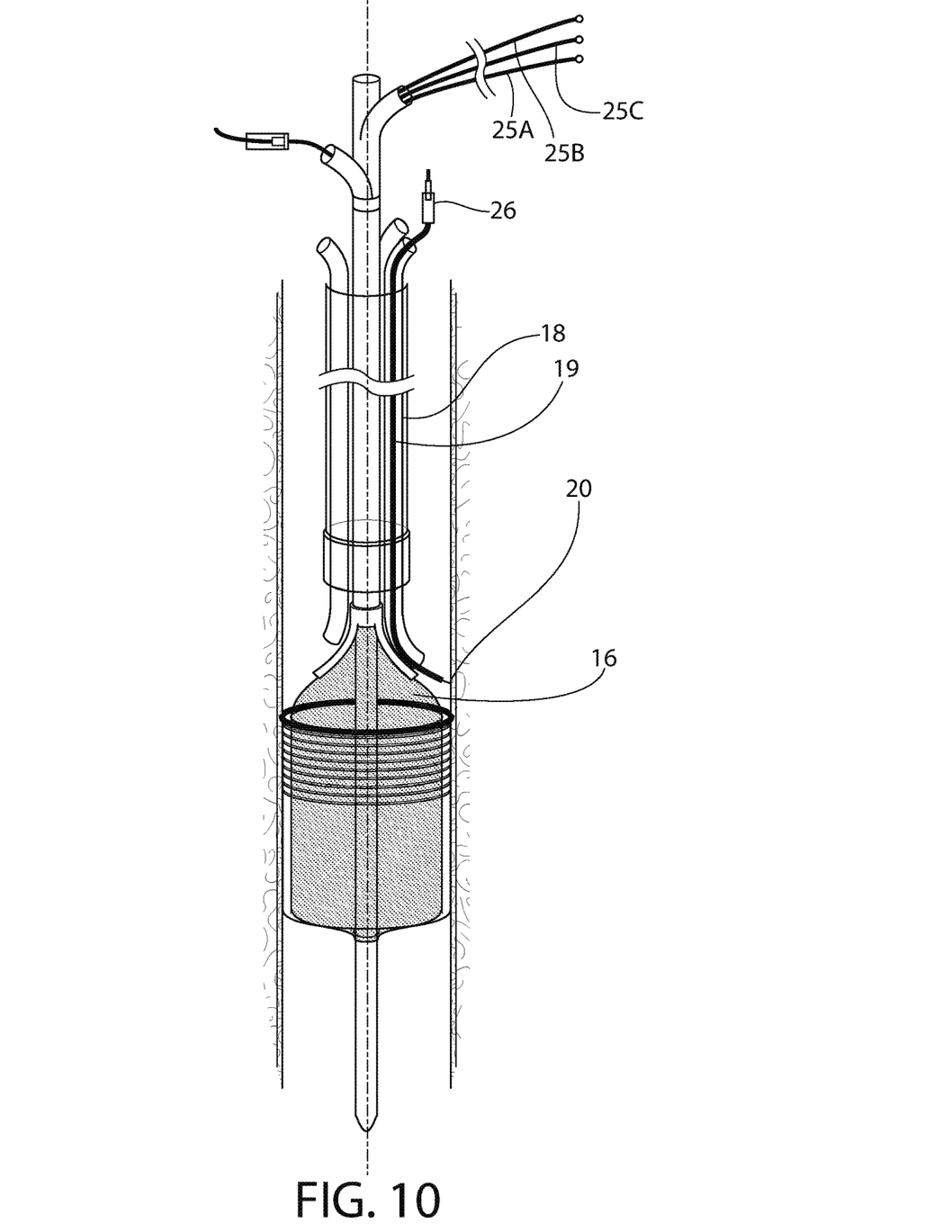

FIG. 10 illustrates threads 25 A, B, and C completely pulled out of the catheter with balloon 16 inflated and injection catheter 19 in guiding tube 18 with needle 20 drawn to penetrate the esophageal wall muscular layer 9. Syringe 26 pumps toxin so it is injected through needle 20. This operation is repeated three times in each of the 3 guiding tubes then the catheter can be rotated and the same operation can be repeated once or twice depending on the diameter of the esophagus so that 6 infections (for smaller diameter GARDs with a small circumference of the ring) up to 9 injections of botulinum toxin (for larger diameter GARDs with a larger circumference of the ring) can be performed at the exact depth in the muscular layer of the esophagus and at equidistance around the circumference of the esophagus above the deployed GARD ring.

Figure 11:
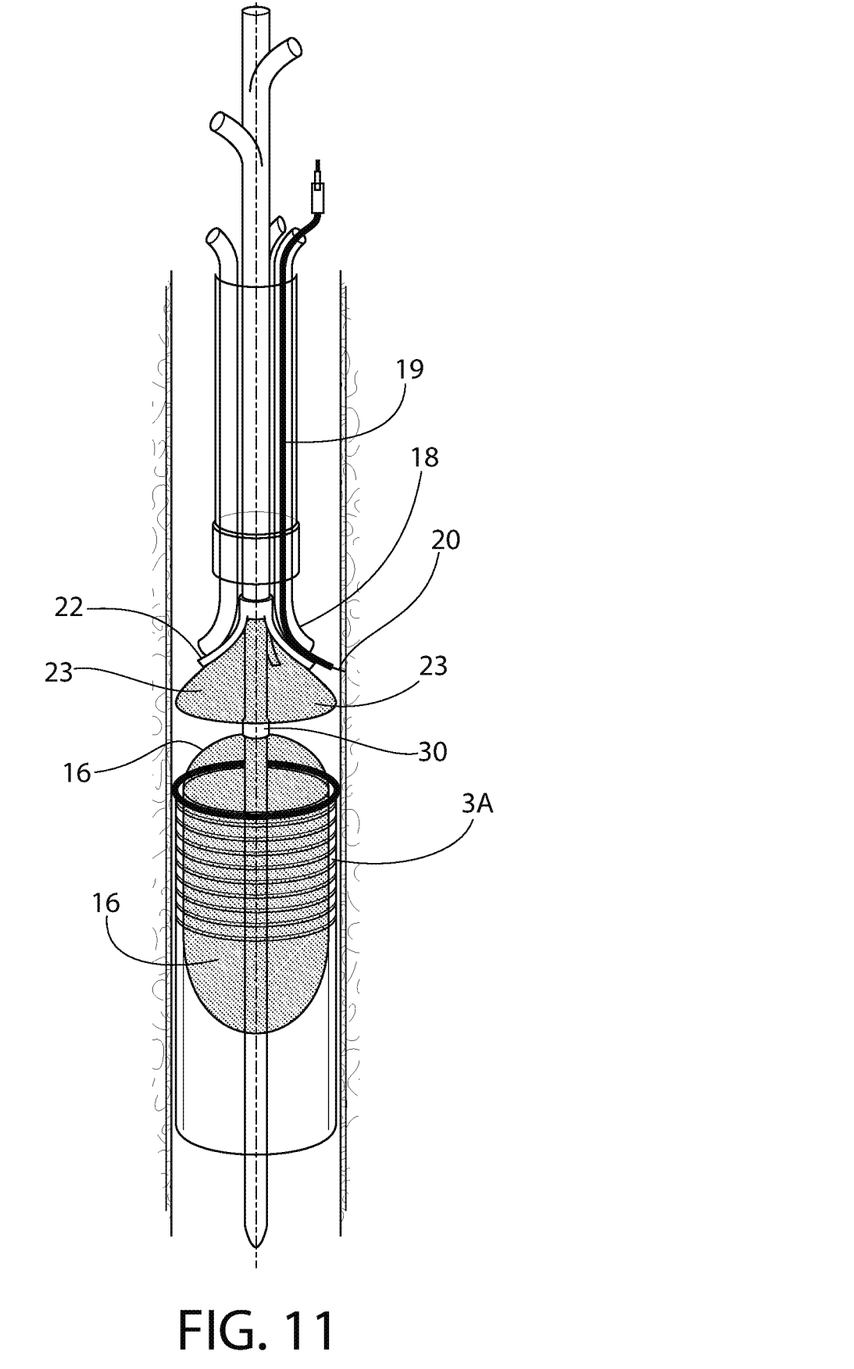

FIG. 11 illustrates a combination of a top small triangular, or conical balloon 23 used to spread the arms of the arm expander 22 and the guiding tube 18 and a bottom oval balloon 16 to help deploy the ring of the GARD. A stopper 30 in the middle of both balloons separates both balloon and prevents the folded ring (not shown folded) to move upwards when the threads are pulled out (see FIG. 10) during deployment of the ring 3A. The distance between the injection needle and the upper limit of the ring of the GARD should be in the order of 1 cm to 2 cm, preferably 1 cm so the botulinum toxin acts at its best to prevent migration of the GARD ring. If necessary, the oval balloon can be deflated once the GARD ring is deployed and the device pushed down a few centimeters so that the small triangular or rather conical balloon is right above the ring 3A (not shown) and the injection of botulinum are even closer to the top part of the GARD ring.

Botulinum toxin is a neurotoxic protein produced by the bacterium *Clostridium botulinum* and related species. It prevents the release of the neurotransmitter acetylcholine from axon endings at the neuromuscular junction and thus causes flaccid paralysis of the muscles. Botulinum toxin also paralyzes smooth muscles as well as striated muscles.

Botulinum toxin, particularly type A, is already widely used in medicine and sold as BoTox® by Allergan, Dysport® by Ipsen Pharma and Xeomin by Merz Pharmaceuticals for treatment of muscular blockage in the eye for blepharospasm, bladder hyperactivity, cervical dystonia, chronic migraine, focal limb spasticity, and for face wrinkles.

According to the invention botulinum toxin can be injected in very small volumes, in the order of 0.1 ml to 0.4 ml, which is desirable for injection in a very narrow area of esophageal muscle about 1 mm to 2 mm thick (about 0.04 to 0.08 inches)

To avoid injecting potentially toxic botulinum toxin through the wall of the esophagus, an injection device incorporated or clipped on the delivery system used to place the GARD in the esophagus or an independent injection device from the catheter used to place the GARD in the esophagus is used to inject the botulinum toxin around the inner circumference of the esophagus at a precise depth in the wall of the esophagus.

The injection device consists of a balloon that is inflated when in position with three "guiding" tubes placed at 120 degrees of each other around the 360 degree circumference. Once inflated, when the balloon is in contact with the wall of the esophagus, the exact angle of the guiding tube and the wall of the esophagus can be determined precisely as the end portion of the guiding tubes is glued to the top part of an hexagonal shaped balloon or better placed on an "balloon expander" made of a ring and 3 "legs" that are spread by the inflated balloon. An injection catheter obtained commercially (Olympus Needlemaster™ needles, Boston Scientific Interject™, Cook Medical AcuJect™) is passed through the guiding tubes until the catheter reaches the esophageal wall. Since the angle between the catheter with the needle and the wall of the esophagus depends on the diameter of the esophagus that conditions the volume of air used to inflate the balloon and the diameter of the ring of the GARD device used for a given patient, the exact depth of injection can be calculated for each diameter of GARD ring and the appropriate catheter with needle length, normally between 3 mm and 6 mm long can be chosen in advance so as to inject at a 2 mm depth in the muscular layer of the esophagus in order to inject the botulinum toxin blindly through the esophageal wall into the muscular layer of the esophagus, avoiding injections in the mucosa or submucosa that is too proximally which can cause esophageal mucosal lesions or too deep through the wall of the esophagus that can lead to mediastinitis with cases of deaths reported (See Complications of botulinum toxin injections for treatment of esophageal motility disorders, van Hoeij F B, et al., Dis Esophagus 2017 Feb. 1; 30(3):1-5). Also, using fluoroscopy can help assess the good position of the injection catheter and the depth of the needle in the wall of the esophagus.

The regular disposition every 120 degrees of the guiding tubes allows injections at 3 equidistant locations around the circumference of the esophagus. The balloon is then deflated, the catheter turned 40 degrees and then reinflated with 3 more injections. In larger size diameters of the GARD ring as in 30 mm, the operation is repeated a third time as the circumference of the esophagus will be approximately 90 mm so 9 injections of 10 units of botulinum toxin for a total of 90 Units is used, while in a smaller 20 mm diameter of GARD, a 60 degree rotation once with 6 injections is sufficient as the circumference is about 60 mm and 6 injections of 10 to 15 units of botulinum toxin is sufficient.

Botulinum toxin injection into the gastroesophageal junction of the esophagus is used for more than 20 years to treat patients who have achalasia and non-cardiac chest pain with non-reflux, nonachalasia spastic esophageal motor disorders and studies have demonstrated efficacy in relieving pain (see "Botulinum toxin for achalasia" by Pasricha et al in the Lancet 341:244-245, 1993 and "Treatment of chest pain in patients with noncardiac, nonreflux, nonachalasia spastic esophageal motor disorders using botulinum toxin injection into the gastroesophageal junction by Larry S Miller et al. in the American Journal of Gastroenterology 97, 1640-1646 (2002)).

As Botulinum toxin is a potential toxic compound, the use of an injection guide to help the endoscopist inject the botulinum toxin at the selected, right location and at a selected depth to reach the muscular layer of the esophagus mitigates the potential risks of botulinum toxin injections.

Also, it is known that botulinum toxin injection will last for up to one year which is more than sufficient for the first generation DM-GARD that will be used up to 4 weeks then replaced after 1 month by the Therapeutic-GARD and Obesity-GARD that will include features in addition to the botulinum toxin to help keep the devices in place for longer periods of time.

EP 2729162 B1 assigned to Allergan, Inc., describes treating two conditions, Diffuse Esophageal Spasm (DES) and "Nutcracker esophagus," with Botox A injections in the esophagus.

The present invention comprises injecting Botulinum toxin A in the muscular layer of the body of the esophagus right above the ring of the GARD, not all along the length of the esophagus as needed for DES and Nutcracker which the procedure described in the Allergan patent. Allergan's patent does not describe using Botox A to prevent migration of a medical device like the GARD.

Botulinum toxin A will not be used for injections in the esogastric junction as used in achalasia but exclusively in association with medical devices to diagnose and treat GERD, LPR and obesity above the esogastric junction in the lower third of the esophagus and preferably about 3 cm to 5 cm above the Z line which is the limit of the gastric mucosa and the esophageal mucosa at the esogastric junction.

The balloon element of the system has two functions, first to help deploy the GARD ring and stabilize the guiding tubes thanks to the balloon expander before botulinum toxin injection and second to enable exact placement of the delivery catheter with the balloon in the center of the esophagus which in turn enables appropriate placement of the guiding tubes in the correct direction and right angle to control depth of botulinum toxin injection precisely into the muscular layer of the esophagus that is 2 mm deep while operating at a distance of about 1 meter (or about 3 feet) away. The injection is made about 1 cm above the upper ring of the GARD with a purging volume in the catheter of approximately one milliliter and a controlled length of the needle of 3 mm to 6 mm when taken out of the protection sheath at endoscopy using a 21 to 25 gauge needle, preferably a 23 gauge needle, that will reach both smooth muscle layers of the esophagus to avoid injecting the toxin at another location either too proximally in the mucosa or submucosa of the esophagus or too distally beyond the esophagus as the botulinum toxin can be very toxic even at very low dose.

EXAMPLES

As an example, a total volume of 1 ml of solvent will be used in a 100-Unit vial of Botox or Xeomin so that each 0.1 ml of solution contains 10 Units of botulinum toxin. Once the catheter is purged with the solution outside the body of the patient, there should be at least 1 ml of the botulinum toxin ready for injection in the syringe after purging the catheter with the botulinum solution. At about 1 cm above the ring, 0.1 ml to 0.15 ml corresponding to 10 U to 15 U should be injected at 6 to 9 sites of equal distance around the circumference of the esophagus for a total of about 90 units of botulinum toxin. To help the endoscopist proceed with the injection, a catheter with 3 injection tubes will help guide the injection catheter at a pre-determined angle of penetration of the esophageal wall depending on the inflation of the balloon, which will help determine the depth of injection. Also, the use of fluoroscopy can help guarantee injection in the esophageal wall and in the proper muscular layer of the esophageal wall. The preferred botulinum toxin for injection used is Xeomin by Merz where 1 ml of NaCl 0.9% is used to reconstitute the solution then injected in an Olympus endoscopic injection catheter. However, other brands of botulinum toxins can be used as well as other catheter and dosages.

The present invention, therefore, is well adapted to carry out the objectives and attain the ends and advantages mentioned, as well as others inherent therein. While the invention has been depicted and described and is defined by reference to particular embodiments of the invention, such references do not imply a limitation on the invention, and no such limitation is to be inferred. Consequently, the invention is intended to be limited only by the spirit and scope of the appended claims, giving full cognizance to equivalents in all respects.

What is claimed is:

1. A method of preventing contraction and peristaltic wave action of an esophagus of a patient causing displacement of a gastroesophageal anti-reflux device having a ring used to diagnose and manage refractory Gastroesophageal Reflux Disease (GERD) from an intended location in the esophagus towards or into the stomach comprising injecting botulinum toxin in the wall of the esophagus immediately above where the ring will be placed to prevent contraction and peristaltic wave action of the esophagus.

2. The method of claim 1 wherein said device is a first medical device designed for short term placement, and wherein said method further comprises determining if the first medical device functions as intended and then, after the determination, replacing the first medical device with a second medical device designed to function for a long term, each of the medical devices adapted to treat GERD and/or obesity.

3. The method of claim 1 wherein the device is placed in the esophagus to treat GERD and/or Laryngo-Pharyngeal Reflux (LPR) in the patient.

4. The method of claim 1 wherein the device is placed in the esophagus to treat obesity associated with GERD in the patient.

5. The method of claim 4 wherein the device is introduced with the ring folded and kept folded with a suture tied with a draw hitch knot which can be untied from a distance by pulling on a thread of the suture to release the ring so that the ring unfolds.

6. The method of claim 1, wherein the device is used to diagnose and manage GERD after sleeve gastrectomy for obesity.

* * * * *